(12) United States Patent
Landy et al.

(10) Patent No.: US 9,964,524 B2
(45) Date of Patent: May 8, 2018

(54) METHOD AND AN APPARATUS FOR BOLT INSPECTION

(71) Applicant: Siemens Energy, Inc., Orlando, FL (US)

(72) Inventors: James F. Landy, Cape Canaveral, FL (US); Thomas F. Quinn, Winter Springs, FL (US); Daniel R. Ryan, Stanley, NC (US); Derrick Marcantel, Oviedo, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 294 days.

(21) Appl. No.: 14/751,187

(22) Filed: Jun. 26, 2015

(65) Prior Publication Data

US 2016/0377578 A1 Dec. 29, 2016

(51) Int. Cl.
*G01N 29/265* (2006.01)
*G01N 29/04* (2006.01)

(52) U.S. Cl.
CPC ......... *G01N 29/265* (2013.01); *G01N 29/043* (2013.01); *G01N 2291/0234* (2013.01); *G01N 2291/0289* (2013.01); *G01N 2291/2691* (2013.01)

(58) Field of Classification Search
CPC .............................................. G01N 2291/2691
See application file for complete search history.

(56) References Cited

U.S. PATENT DOCUMENTS

| 4,062,227 | A | * | 12/1977 | Heyman | G01B 17/04 73/579 |
| 5,095,753 | A | * | 3/1992 | Russ | G01N 29/223 73/598 |
| 5,721,380 | A | * | 2/1998 | Gozlan | G01N 29/223 73/761 |
| 5,970,798 | A | * | 10/1999 | Gleman | G01L 5/246 73/761 |

\* cited by examiner

*Primary Examiner* — Paul West
*Assistant Examiner* — Mark A Shabman

(57) ABSTRACT

A method and an apparatus for bolt inspection are presented. The bolt has a cylindrical threaded surface delimited by a pair of end faces that are opposite to each other. An ultrasonic transducer device contacts one of the pair of end faces for performing a scan operation. A guide structure is engaged with the bolt that guides a motion of the ultrasonic transducer device such that only a portion of a transducer contact surface contacts the one of the pair of end faces during the scan operation. The guide structure delimits a radial extent of the motion of the ultrasonic transducer device during the scan operation.

9 Claims, 4 Drawing Sheets

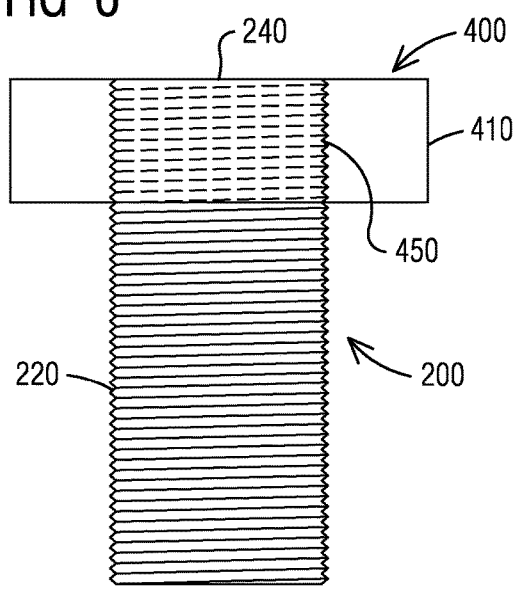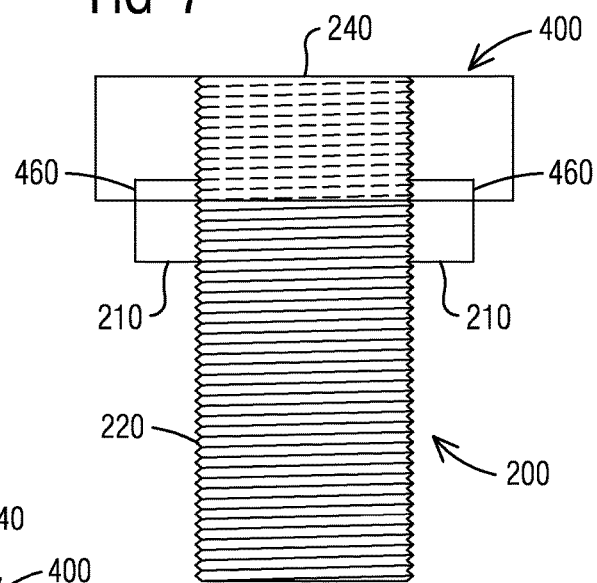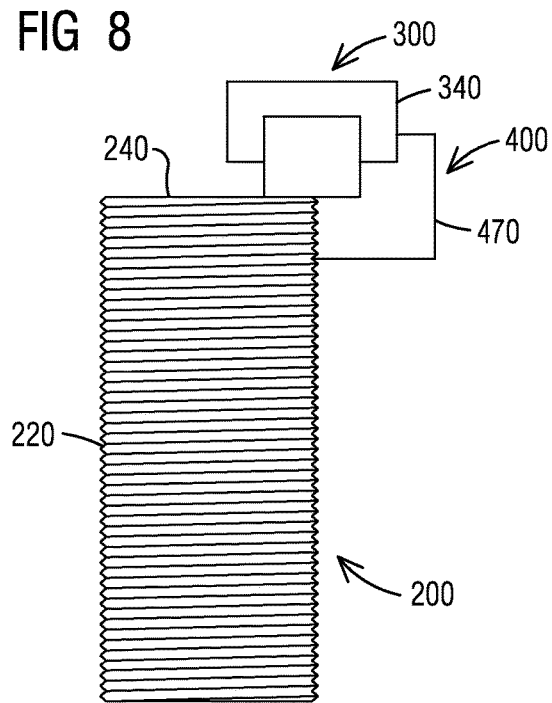

METHOD AND AN APPARATUS FOR BOLT INSPECTION

FIELD

Aspects of the present invention relate to a method and an apparatus for bolt inspection.

DESCRIPTION OF RELATED ART

It is known that a structural flaw, such as a crack, may occur in a component of power machinery, such as a compressor bolt. The structural flaw of the component may progressively grow to a sufficiently large size which could lead to a failure event of the component. The failure of the component may potentially result in a costly damage and downtime of the power machinery.

The current techniques for bolt inspection solely rely on inspectors capabilities through experience and training. A key area for the bolt inspection is a minor diameter thread root of the bolt where a structure flaw tends to initiate. Complete inspection coverage of this area allows for smallest cracks to be detected during inspection. This may benefit customers and provide a superior quality of bolt inspection.

SUMMARY

Briefly described, aspects of the present invention relate to a method and an apparatus for bolt inspection.

According to an aspect, a method for inspecting a bolt, the bolt comprising a cylindrical threaded surface delimited by a pair of end faces that are opposite to each other, comprises positioning an ultrasonic transducer device contacting one of the pair of end faces of the bolt. A scan operation is performed by guiding a motion of the ultrasonic transducer device along the one of the pair of end faces of the bolt such that only a first portion of a transducer contact surface contacts the one of the pair of the end faces of the bolt during the scan operation. The motion of the ultrasonic transducer device is guided by a guide structure that delimits a radial extent of the motion of the ultrasonic transducer device during the scan operation.

According to another aspect, an apparatus for inspecting a bolt comprises an ultrasonic transducer device and a guide structure. The bolt comprises a cylindrical threaded surface delimited by a pair of end faces that are opposite to each other. The ultrasonic transducer device contacts one of the pair of the end faces for performing a scan operation. The guide structure guides a motion of the ultrasonic transducer device along the one of the pair of the end faces of the bolt such that only a first portion of a transducer contact surface contacts the one of the pair of the end faces of the bolt during the scan operation. The guide structure delimits a radial extent of the motion of the ultrasonic transducer device during the scan operation.

Various aspects and embodiments of the application as described above and hereinafter may not only be used in the combinations explicitly described, but also in other combinations. Modifications will occur to the skilled person upon reading and understanding of the description.

BRIEF DESCRIPTION OF THE DRAWINGS

Exemplary embodiments of the application are explained in further detail with respect to the accompanying drawings. In the drawings:

FIG. 6 illustrates a perspective side view of a guide structure according to an embodiment;

FIG. 7 illustrates a perspective side view of a guide structure according to an alternative embodiment;

FIG. 8 illustrates a perspective side view of a guide structure according to another alternative embodiment;

To facilitate understanding, identical reference numerals have been used, where possible, to designate identical elements that are common to the figures.

DETAILED DESCRIPTION OF INVENTION

A detailed description related to aspects of the present invention is described hereafter with respect to the accompanying figures.

Figure 1:
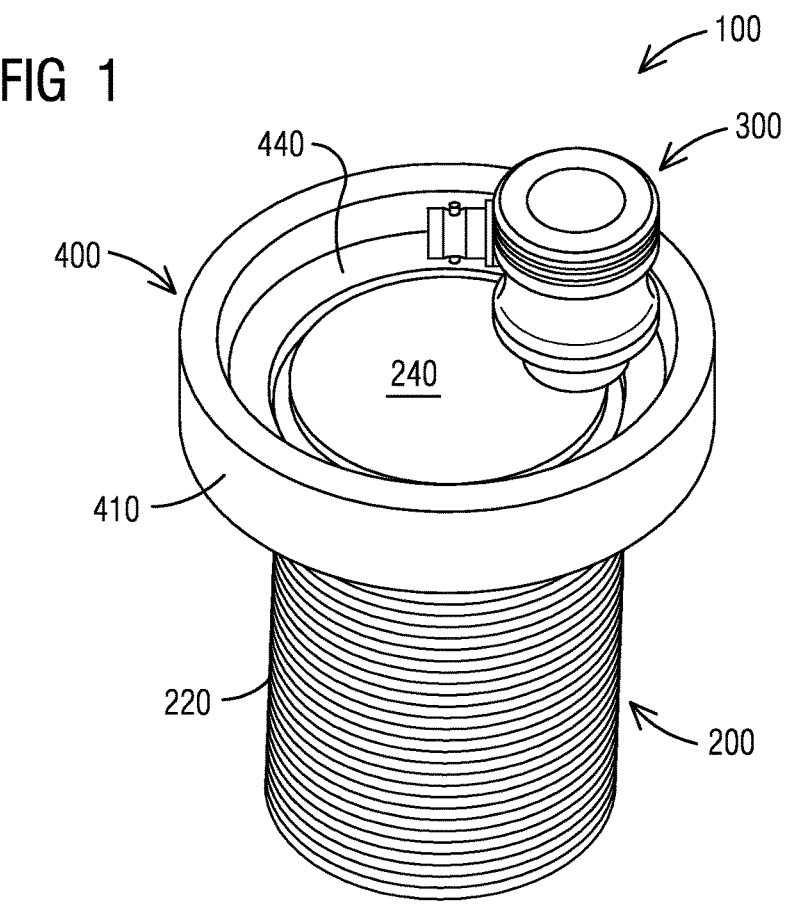
FIG. 1 illustrates a perspective view of an apparatus for bolt inspection according to an embodiment.
Figure 2:
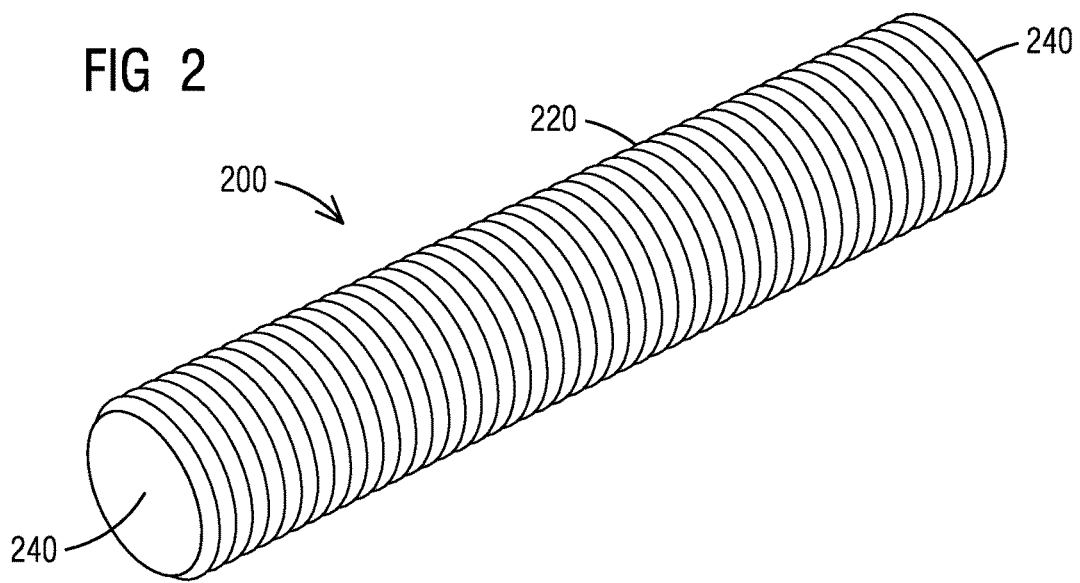
FIG. 2 illustrates a perspective view of a bolt according to an embodiment.
Figure 3:
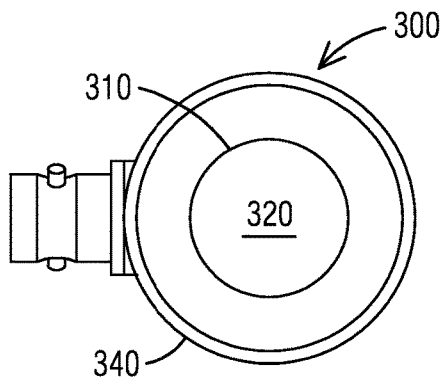
FIG. 3 illustrates a perspective top view of an ultrasonic transducer device according to an embodiment.
Figure 4:
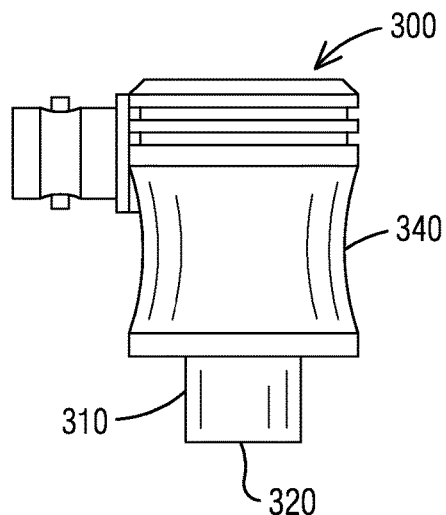
FIG. 4 illustrates a perspective side view of an ultrasonic transducer device according to an embodiment.

FIG. 1 illustrates a perspective view of an apparatus 100 for inspecting a bolt according to an embodiment. According to the illustrated embodiment, the apparatus 100 comprises an ultrasonic transducer device 300 that may be used for performing a standard or longitudinal wave inspection on a bolt 200. As shown in FIG. 2, the bolt 200 is, in this example, a large diameter bolt having a cylindrical threaded surface 220 delimited on either end by a respective circular end face 240. An exemplary ultrasonic transducer device 300 is illustrated in FIG. 3 and FIG. 4 which illustrate a top view and a side view respectively of the ultrasonic transducer device 300. As shown, the ultrasonic transducer device 300 comprises a generally cylindrically shaped electro-acoustic transducer 310. In the illustrated example, the electro-acoustic transducer 310 is a cylindrical shaped piezoelectric crystal, arranged inside a housing 340 and having a contact surface 320 which is meant to contact a surface of the component to be inspected.

Referring back to FIG. 1, during a bolt inspection, the ultrasonic transducer device 300 may be arranged such that a portion of the contact surface 320 of the transducer 310 contacts one of the end faces 240 of the bolt 200. The apparatus 100 further comprises a guide structure 400 that guides a motion of an ultrasonic transducer device 300 during a scan operation. In particular, the guide structure 400 delimits a radial extent of the motion of the ultrasonic transducer device 300 device during the scan operation. This allows an operator to reliably scan even the edges of the circular end face 240, so as to be able to pick up even relative smaller and peripheral flaws, e.g. small cracks originating in a minor diameter of the bolt 200.

Figure 5:
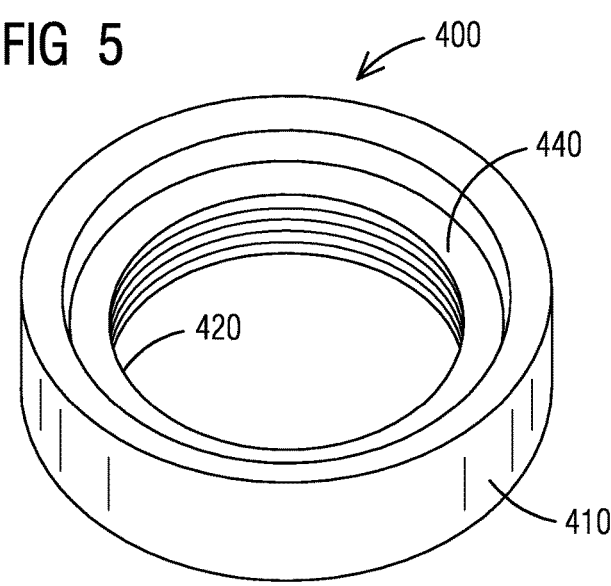
FIG. 5 illustrates a perspective view of a guide structure according to an embodiment.

In the example embodiment of FIG. 1 and an example embodiment of FIG. 5, the guide structure 400 includes a hollow cylindrical body 410. From an inner surface of the hollow cylindrical body 410, an annular shaped flange 420 extends in a radially inward direction, being concentric to the hollow cylindrical body 410. The annular flange 420 may be provided, for example at or proximate to one of the axial ends of the hollow cylindrical body 410. The annular flange 420 defines a land area 440, which is essentially a flat annular surface. As shown in FIG. 1, the guide structure 400 may be arranged concentrically around the bolt 200 such that the land area 440 circumscribes the end face 240 on which the scan is to be performed.

According to an embodiment as illustrated in FIG. 6, a guide structure 400 may comprise an internal threading 450 on the cylindrical body 410. The internal threading 450 of the guide structure 400 may engage with threading of a cylindrical threaded surface 220 of the bolt 200 so that the guide structure 400 is secured in a fixed position to the bolt 200 during a scan operation along an end face 240 of the bolt 200.

According to an alternate embodiment as illustrated in FIG. 7, a guide structure 400 may comprise a magnetic element 460. The magnetic element 460 of the guide structure 400 may engage with a metallic element 210, for example, a metallic nut, disposed along a defined axial length of the bolt 200 so that the guide structure 400 is secured in a fixed position to the bolt 200 during a scan operation along an end face 240 of the bolt 200.

According to yet another embodiment as illustrated in FIG. 8, instead of a cylindrical body with an annular flange, a guide structure 400 may comprise an attachment element 470, for example, a clip. The attachment element 470 of the guide structure 400 may be affixed to an ultrasonic transducer device 300, such as a housing 340 of the ultrasonic transducer device 300, so that the guide structure 400 may engage slidingly with a cylindrical threaded surface 220 of the bolt 200 during a scan operation along an end face 240 of the bolt 200.

An exemplary bolt inspection method is now described. In the illustrated embodiment prior to inspecting a bolt 200, a cylindrical threaded surface 220 of the bolt 200 is cleaned so as to show no signs of galling. A guide structure 400, as illustrated in FIG. 5, is then arranged on the bolt 200 such that a flat horizontal surface of a land area 440 of the guide structure 400 circumscribes the end face 240 and is at the same level as the end face 240 of the bolt 200.

Subsequently, the ultrasonic transducer device 300 is arranged on the end face 240 and the scanning operation is started wherein the transducer device 300 is continuously maneuvered along the surface of the end face 240, all the while ensuring that at least a portion of the contact surface 320 of the piezoelectric crystal 310 is in contact with the end face 240 of the bolt 200. In particular, when scanning the peripheral edges of the circular end face 240, the guide structure 400 delimits the radial extent of the movement of the ultrasonic transducer device 300. An inventive feature provided by the guide structure 400 is that it makes it possible to carry out an ultrasonic scan with only a portion of the contact surface 320 of the piezoelectric crystal 310 contacting the end face 240 of the bolt 200, while the remaining portion of the contact surface 320 contacts the land area 440. A scan operation may refer to an amplitude modulation scan to detect a presence of a flaw in the bolt 200. A flaw of the bolt 200 may refer to a crack of the bolt 200.

According to an embodiment, a full length of a bolt 200 may be inspected. An inspection may require separate scan operations along an end face 240 of a bolt 200 to complete the full length inspection with a required detectability. The separate scan operations may consist of a backwall exam, a near side exam, a far side exam, and a far side exam enhanced. According to an embodiment, prior to inspection, the ultrasonic transducer device 300 should be calibrated for performance. The scan operation will detect root cracks from a minor diameter of a bolt 200.

Figure 9:
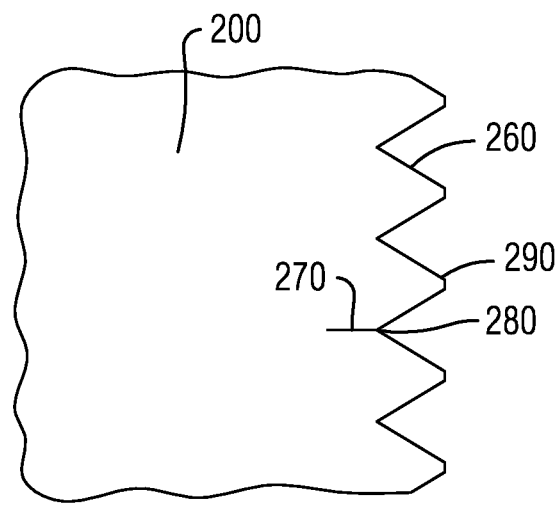
FIG. 9 illustrates a perspective view of a cross section of a bolt to be inspected according to an embodiment.

FIG. 9 illustrates a perspective view of a cross section of a bolt 200 to be inspected according to an embodiment. According to the illustrated embodiment, a bolt 200 may comprise threading 260, a minor diameter 280, a major diameter 290. A minor diameter 280 of the bolt 200 may refer to a root area of the bolt 200. As illustrated in FIG. 9, a key critical area of a bolt inspection may refer to a minor diameter 280 of the bolt 200 where a structure flaw, such as a root crack 270, tends to initiate.

The land area 440 of a guide structure 400 may be determined based on a number of parameters to ensure an inspection coverage area and detectability in a minor diameter 280 of the bolt 200. These parameter may comprise, for example, a minimum size of a flaw to be inspected for a bolt 200, the minor diameter 280 of the bolt 200, the major diameter 290 of the bolt 200, a dimension of a contact surface 320 of an ultrasonic transducer device 300, a dimension of a housing 340 of an ultrasonic transducer device 300, or any combinations thereof.

Figure 10:
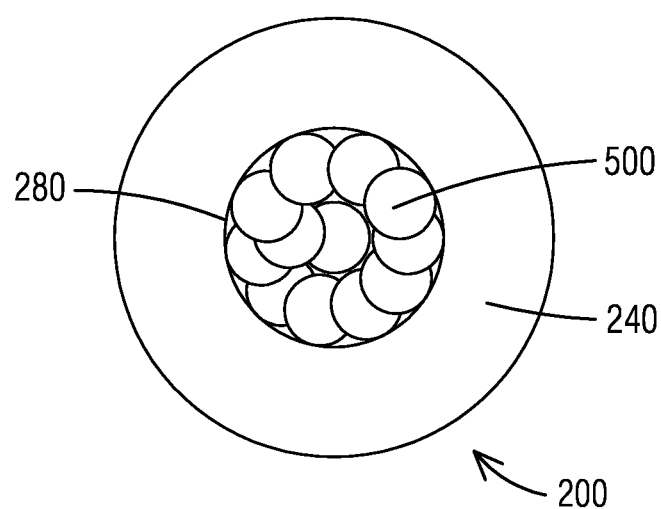
FIG. 10 illustrates a schematic view of multiple overlapping scan operations of bolt inspection according to an embodiment.

According to an aspect of the invention, inspection of an entire cross section of a minor diameter 280 of a bolt 200 may be implemented by multiple overlapping scan operations. FIG. 10 illustrates a schematic view of multiple overlapping scan operations of bolt inspection according to an embodiment. As illustrated in FIG. 10, multiple scan operations, illustrated by circles 500, may be performed along an end face 240 of a bolt 200. Each of the multiple scan operations 500 may be overlapped to each other. According to an embodiment, the multiply overlapping scan operations may ensure an inspection of an entire cross section of a minor diameter 280 of a bolt 200.

According to an aspect, the illustrated embodiments may provide adequate bolt surface inspection coverage. The illustrated guide structure 400 may allow a contact surface 320 of an ultrasonic transducer device 300 to rest on an edge of an end face 240 of a bolt 200 during a scan operation without a loss of inspection signal. A critical dimension of a land area 440 of a guide 440 may allow for the smallest possible cracks to be detected when a contact surface 320 of an ultrasonic transducer device 300 is at an outer edge of an end face 240 of a bolt 200. Without the use of a guide structure 400, crack detection capabilities for a bolt 200 are substantially reduced.

According to an aspect, the illustrated guide structure 400 may serve as a levee system to a couplant. This may allow for constant coupling to a bolt face 240 during bolt inspection.

According to an aspect, the illustrated embodiments may be used to inspect a compressor bolt of power machinery. According to an aspect, the inspection may cover a full length of a bolt ultrasonic inspection. The illustrated bolt inspection may be performed during cover lifts of a compressor section or during a major outrage when a rotor is removed from a power machinery unit. Access may be required to a bolt end that resides between compressor ends.

The disclosed method and the apparatus may be implemented to a plurality of different types of power machinery, such as gas turbines, steam turbines, or wind turbines, etc.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

LIST OF REFERENCES

100 Bolt Inspection Apparatus
200 Bolt
210 Metallic Element of a Bolt
220 Cylindrical Threaded Surface of a Bolt
240 End Face of a Bolt
260 Threading on a Cylindrical Threaded Surface of a Bolt
270 Root Crack at Minor Diameter of a Bolt
280 Minor Diameter of a Bolt
290 Major Diameter of a Bolt
300 Ultrasonic Transducer Device
310 Electro-acoustic Transducer
320 Contact Surface of an Ultrasonic Transducer device
340 Housing of an Ultrasonic Transducer Device
400 Guide Structure
410 Hollow Cylindrical Body of a Guide Structure
420 Annual Flange of a Guide Structure
440 Land Area of a Guide Structure
450 Internal Threading of a Guide Structure
460 Magnetic Element of a Guide Structure
470 Attachment Element of a Guide Structure
500 Scan Operations

What is claimed is:

1. A method for inspecting a bolt, the bolt comprising a cylindrical threaded surface delimited by a pair of end faces opposite to each other, the method comprising:
    positioning an ultrasonic transducer device contacting one of the pair of the end faces of the bolt; and
    performing a scan operation by guiding a motion of the ultrasonic transducer device along the one of the pair of the end faces of the bolt such that only a first portion of a transducer contact surface contacts the one of the pair of the end faces of the bolt during the scan operation,
    wherein guiding the motion of the ultrasonic transducer device comprises arranging a guide structure secured in a fixed position to the bolt that delimits a radial extent of the motion of the ultrasonic transducer device,
    wherein the guide structure comprises a hollow cylinder having an annular flange defining a land area extending concentrically around the bolt, and
    wherein a second portion of the transducer contact surface contacts the land area during the scan operation.

2. The method according to claim 1, wherein a dimension of the land area is determined by a parameter selected from the group consisting of: a minimal dimension of a flaw to be inspected, a dimension of a housing of the ultrasonic transducer device, a dimension of the transducer contact surface, a major diameter of the bolt, a minor diameter of the bolt, and combinations thereof.

3. The method according to claim 1, wherein the guide structure comprises internal threading that engages with threading of the bolt to secure the guide structure in a fixed position during the scan operation.

4. The method according to claim 1, wherein the guide structure comprises a magnetic element configured to engage with a metallic element disposed along a defined axial length of the bolt to secure the guide structure in a fixed position during the scan operation.

5. The method according to claim 1, wherein the guide structure comprises an attachment element affixed to a transducer housing that engages slidingly with the cylindrical threaded surface of the bolt.

6. The method according to claim 1, wherein the inspection comprises determining a flaw on a minor diameter of the bolt during the scan operation.

7. The method according to claim 1, wherein the transducer contact surface is circular.

8. The method according to claim 1, wherein the ultrasonic transducer device includes a piezoelectric crystal, and wherein the transducer contact surface is a surface of the piezoelectric crystal.

9. The method according to claim 1, further comprising performing multiple individual overlapping scan operations along the one of the pair of the end faces of the bolt to inspect an entire cross section of a minor diameter of the bolt.

* * * * *